United States Patent [19]

Haskell

[11] 4,012,289
[45] Mar. 15, 1977

[54] N-BUTANE/ACETONE SEPARATION USING SULFOLANE

[75] Inventor: Donald M. Haskell, Bartlesville, Okla.

[73] Assignee: Phillips Petroleum Company, Bartlesville, Okla.

[22] Filed: Oct. 14, 1975

[21] Appl. No.: 621,886

[52] U.S. Cl. .................................. 203/51; 203/58; 203/62
[51] Int. Cl.² ...................... B01D 3/34; B01D 3/40
[58] Field of Search ................ 203/51, 58, 62, 78; 202/154; 208/311, 321, 325; 260/676 R, 676 AD

[56] References Cited

UNITED STATES PATENTS

| 2,360,859 | 10/1944 | Evans et al. | 208/325 X |
| 2,360,861 | 10/1944 | Pierotti et al. | 203/51 X |
| 2,455,803 | 12/1948 | Pierotti | 203/51 X |
| 3,232,849 | 2/1966 | Renberg | 203/51 |

Primary Examiner—Norman Yudkoff
Assistant Examiner—Dale Lovercheck

[57] ABSTRACT

A mixture of n-butane and acetone is effectively separated by liquid-liquid extraction or extractive distillation using a sulfolane as the extractive solvent.

8 Claims, 1 Drawing Figure

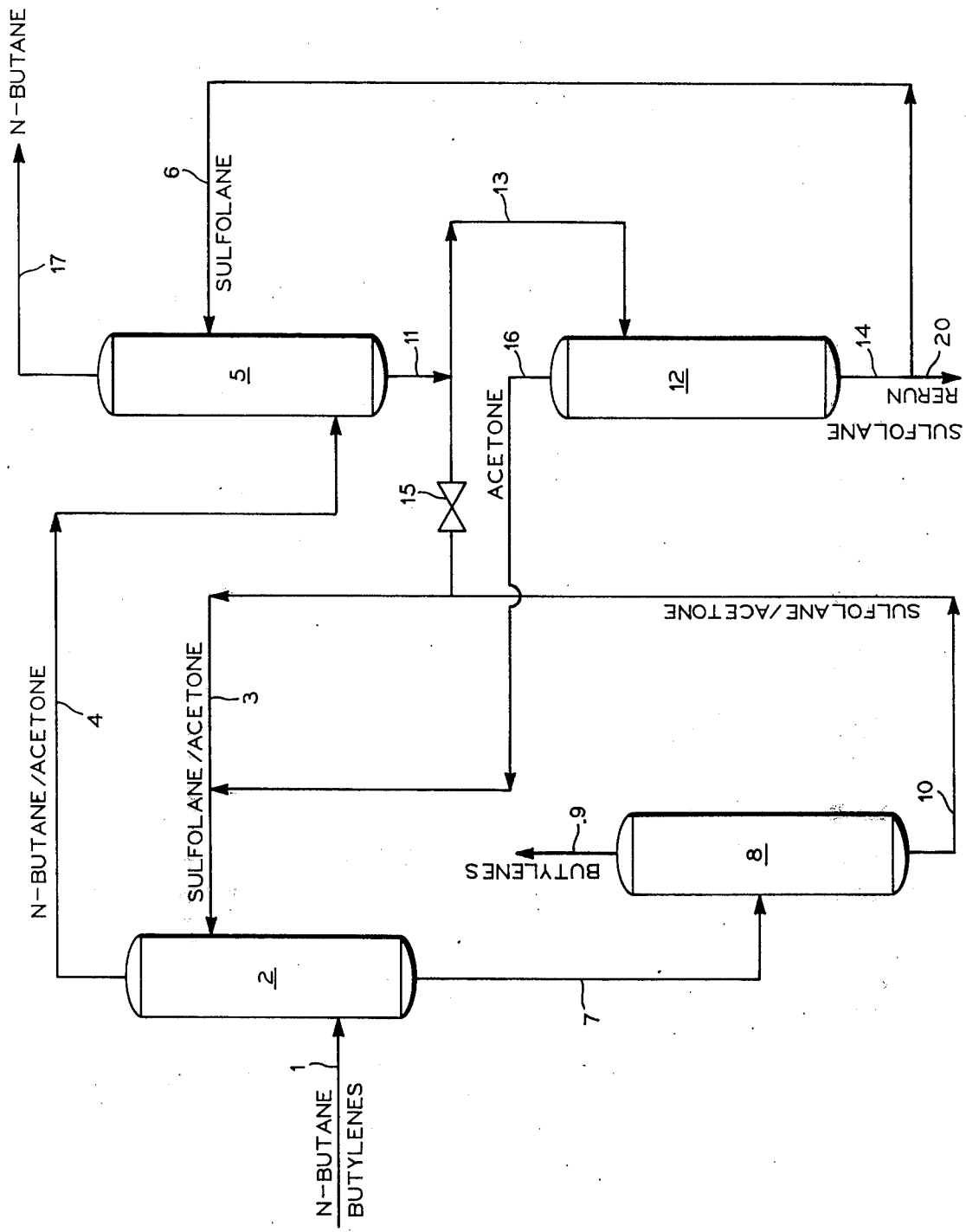

N-BUTANE/ACETONE SEPARATION USING SULFOLANE

This invention relates to the separation of mixtures. In one aspect this invention relates to the separation of a mixture consisting essentially of n-butane and acetone. In another aspect this invention relates to a method for separating a mixture consisting essentially of n-butane and butylenes.

BACKGROUND OF THE INVENTION

In a process for producing butadiene from n-butane employing two dehydrogenation steps, the product of the first dehydrogenation step is essentially a mixture of n-butane and butylenes. For the following dehydrogenation step, it is desirable to separate this mixture so that only the butylenes are introduced into the second dehydrogenation zone. This separation step can be carried out by extractively distilling the n-butane/butylene mixture using as extractive solvent a mixture of a sulfolane and acetone. In this extractive distillation, some acetone leaves the distillation column overhead with the n-butane product that also leaves the distillation column overhead. For further processing or recycling of the ingredients, it would be desirable to have a process available by which this mixture of n-butane and acetone can be effectively separated. It is not feasible to separate the n-butane and acetone by ordinary distillation.

THE INVENTION

It is, therefore, one object of this invention to provide a process for separating a mixture of n-butane and acetone.

A further object of this invention is to provide a process for the separation of a mixture of n-butane and butylenes.

Another object of this invention is to provide a process for separating a mixture of n-butane and butylenes, in which process all of the agents used can be recycled so that the waste of materials and energy is minimized.

Further objects, advantages, details, features and embodiments of this invention will become apparent to those skilled in the art from the following detailed description of the invention, the appended claims and the drawing, which shows a schematic flow diagram for a separation of a mixture of n-butane and butylenes.

In accordance with this invention, I have now found that a mixture of n-butane and acetone can be effectively separated by extracting this mixture utilizing a sulfolane as the extractive solvent, which sulfolane has the general formula

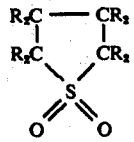

in which the radicals R which can be the same or different are individually selected from the group consisting of hydrogen, alkyl radicals having 1 to 4 carbon atoms, cycloalkyl radicals having 3 to 6 carbon atoms, phenyl, which radicals in turn can be unsubstituted or substituted by alkyl, cycloalkyl and aryl radicals, said sulfolane having 4 to 12 carbon atoms per molecule. By this extraction, an n-butane stream is formed which is essentially free of acetone and a sulfolane stream is formed which contains some acetone. This process has the advantage that the sulfolane used, as well as the acetone which is separated from the mixture, can be reused in the plant that produces the butane/acetone mixture, namely, for the separation of an n-butane/butylenes mixture. "Extraction" as used herein encompasses both liquid-liquid extraction and extractive distillation.

Although the relative quantities of the n-butane/acetone mixture are not critical, and the mixture may contain more acetone, it is presently preferred to carry out the process with a mixture containing about 0.7 to 4.5 weight percent acetone.

In accordance with one embodiment of this invention, the sulfolane phase containing acetone which is produced during the extraction of the n-butane/acetone mixture with the sulfolane as the extractive solvent is separated by fractionally distilling this phase to produce an overhead stream consisting essentially of acetone and a bottom stream consisting essentially of sulfolane. These products can be individually reused and recycled. This the waste of materials and of energy is minimized.

The separation of the n-butane/acetone mixture can be carried out as a liquid-liquid extraction. Although the conditions for this liquid-liquid extraction are not overly critical, it is presently preferred to employ conditions in the following ranges:

| | | |
|---|---|---|
| Temperature of the column: | 70°–140° F. | 21–60° C. |
| Bottom pressure of the column: | 45–105 psig | 0.41–0.83 MPa |
| Top pressure of the column: | 40–100 psig | 0.38–0.79 MPa |
| Flow ratio of sulfolane to n-butane/acetone feed (volume ratio): | 0.33–0.70. | |

In accordance with a further preferred embodiment of this invention, the extraction of the n-butane/acetone mixture with sulfolane is used in a process for separating a stream of a mixture of n-butane and butylenes. In accordance with this embodiment, the mixture of n-butane and butylenes is extractively distilled with an extractive solvent consisting essentially of a mixture of acetone and a sulfolane having the general formula

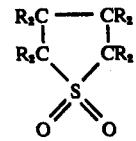

in which the radicals R which can be the same or different are individually selected from the group consisting of hydrogen, alkyl radicals having 1 to 4 carbon atoms, cycloalkyl radicals having 3 to 6 carbon atoms, and phenyl, which radicals R in turn can be unsubstituted or substituted by alkyl, cycloalkyl and aryl radicals, said sulfolane having 4 to 12 carbon atoms per molecule, to produce an overhead stream consisting essentially of n-butane and acetone and a bottom stream consisting essentially of sulfolane, acetone and butylenes. The overhead stream is then further processed, as described above, by extraction utilizing a sulfolane as the extractant. In this embodiment it is presently preferred to use a mixture of sulfolane and acetone as the extractant consisting essentially of 60 to 80 weight percent sulfolane and 40 to 20 weight percent acetone.

The exact conditions for the extractive distillation of the n-butane/butylenes mixture are not overly critical. However, it is presently preferred to operate the distillation column for the n-butane/butylenes mixture under the following conditions:

| | | |
|---|---|---|
| Bottom temperature of the column: | 240°–285° F. | 116–141° C. |
| Bottom pressure of the column: | 55–85 psig | 0.48–0.69 MPa |
| Top temperature of the column: | 115°–140° F. | 46–60° C. |
| Top pressure of the column | 50–75 psig | 0.45–0.62 MPa |
| Volume ratio of the flow of the sulfolane/acetone mixture (extractive solvent) to n-butane/butylene feed: | 2.8 to 5.2. | |

In accordance with presently preferred embodiments of this invention, the following separation and recycling steps are carried out individually or in combination:

The bottom stream from the extractive distillation of the butane/butylenes mixture consisting essentially of sulfolane, butylenes and acetone is fractionally distilled into a butylene stream and a stream comprising sulfolane and some acetone. This stream comprising sulfolane and acetone is recycled as the extractant into the column in which the n-butane/butylenes mixture is extractively distilled.

The sulfolane phase containing some acetone which resulted as a bottom stream from the extractive distillation of the n-butane/acetone mixture using sulfolane as the extractive solvent is fractionated to produce a sulfolane stream and an acetone stream. The acetone stream is reintroduced into the extractive distillation column for the n-butane/butylenes mixture together with the sulfolane/acetone mixture as part of the extractive solvent, and the sulfolane stream is reintroduced as the extractant into the extraction of the n-butane/acetone mixture.

Unsubstituted sulfolane is the presently preferred extractive solvent for the extraction of the n-butane-/acetone mixture and is also the presently preferred solfolane in the sulfolane/acetone mixture used as the extractive solvent for the extractive distillation of the n-butane/butylenes mixture. All R substituents are hydrogen for this embodiment in the formulae given above.

The invention will be more fully understood from the following description of the drawing.

From a dehydrogenation reaction in which butane is partially dehydrogenated, a stream of n-butane and butylene is introduced via line 1 into an extractive distillation column 2. Into the upper portion of this extractive distillation column 2, a stream of sulfolane and acetone is introduced via line 3. From the extractive distillation column 2, a stream consisting essentially of n-butane and acetone is withdrawn overhead via line 4 and introduced as a liquid stream into the lower portion of a liquid-liquid extraction column 5. Into the upper portion of this extraction column 5, a liquid stream of sulfolane is introduced via line 6.

From the bottom of the extractive distillation column 2, a stream consisting essentially of sulfolane, acetone and butylenes is withdrawn via line 7. This liquid stream is introduced into a fractionation column 8. From this fractionation column 8, an overhead stream 9 consisting essentially of butylenes is withdrawn for further dehydrogenation to produce butadiene. From the bottom of this column a stream consisting essentially of sulfolane, but containing some acetone, is withdrawn via line 10 and recycled via line 13 into the extractive distillation column 2.

From the bottom of the extraction column 5, a stream consisting essentially of sulfolane and containing some acetone is withdrawn via line 11. This stream of line 11 is introduced into a distillation column 12 via line 13. A sulfolane stream is withdrawn from this distillation column 12 from the bottom via line 14, part of which can be passed via line 20 to a rerun unit, and the rest is recycled as the extractive solvent to the extraction column 5 via line 6. The overhead acetone stream leaving the distillation column 12 via line 16 is combined with the sulfolane/acetone mixture of line 3, and the resulting mixture is recycled as the extractive solvent to the extractive distillation column 2.

A valve 15 is provided through which either a part of the stream in line 11 can be added to the sulfolane/acetone stream in line 3 or a part of the sulfolane/acetone stream in line 10 can be run through column 12, e.g., in order to rerun the solvent. Valve 15 thus can be used to solve material balance problems.

The following example will illustrate the liquid-liquid extraction of a butane feedstream containing a small quantity of acetone.

EXAMPLE I

Into a liquid-liquid extraction column of 5 feet height (1.52 meters) and an internal diameter of 2 inches (5.1 centimeters) which was packed with ¼-inch (0.635 centimeter) ceramic saddles, a liquid feedstream containing 99 weight percent of n-butane and 0.94 weight percent of acetone was introduced below the packing. Commercial sulfolane containing 2 weight percent of water was introduced below the packing. Thereby a countercurrent flow of the two liquid phases was provided and the solvent extract was removed from the bottom of the column, whereas the hydrocarbon raffinate was removed from the top. The column was operated at room temperature of about 70° F. (21° C.) and under a pressure of 45 psia (3.06 atm). A series of such runs was carried out at different feed rates. The overhead hydrocarbon raffinate was analyzed by gas/liquid chromatography to determine the acetone content. The results obtained are shown in the following table:

| Butane Feed Rate | | Solvent Feed Rate | | Acetone in Hydrocarbon Raffinate, | Continuous |
|---|---|---|---|---|---|
| lb/hr | kg/hr | lb/hr | kg/hr | ppm * | Phase |
| 22.5 | 10.2 | 21.5 | 9.75 | 150 | hydrocarbon |
| 22.5 | 10.2 | 21.5 | 9.75 | 20 | solvent |
| 40.0 | 18.1 | 40.0 | 18.1 | 25 | solvent |

* parts per million

The results of the above-shown table show that only very minor traces of acetone remain in the hydrocarbon raffinate or, in other words, that 99 percent of the acetone is removed from the hydrocarbon phase. In the case where the continuous phase was the sulfolane, the efficiency was even higher, namely 99.9 percent of the acetone contained in the mixture was removed in these runs. For this reason it is presently preferred to carry out the separation process described with the sulfolane being the continuous phase.

The solvent content of the extract was not analyzed. By material balance it would, however, be expected that the bottom stream withdrawn from the column contained about 2 weight percent of acetone in the sulfolane. This solvent would be suitable for makeup for an extractive distillation for separating n-butane and butylenes.

EXAMPLE II

This calculated example is given to show the conditions for an extractive distillation of an n-butane/acetone stream with sulfolane. The conditions for such an extractive distillation are shown in the following table:

| | | |
|---|---|---|
| Column top temperature: | 110–125° F. | (43–52° C.) |
| Column top pressure: | 45–60 psig | (0.41–0.52 MPa) |
| Column bottom temperature | 335–350° F. | (168–177° C.) |
| Column bottom pressure: | 50–65 psig | (0.45–0.55 MPa) |
| Sulfolane/n-butane-acetone volume ratio: | 0.33–0.70 | |
| Hydrocarbon reflux/overhead product weight volume ratio: | 0.1–1.0 | |

Reasonable variations and modifications, which will be apparent to those skilled in the art, can be made in this invention without departing from the spirit and scope thereof.

I claim:

1. A process to separate a first mixture of n-butane and from about 0.7 to 4.5 weight percent acetone, which method comprises
   a. contacting said mixture in a fluid contacting zone with a sulfolane having the formula

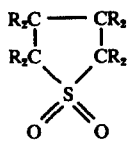

in which the radicals R which can be the same or different are individually selected from the group consisting of hydrogen, alkyl radicals having 1 to 4 carbon atoms, cycloalkyl radicals having 3 to 6 carbon atoms, and phenyl, which radicals R in turn can be unsubstituted or substituted by alkyl, cycloalkyl and aryl radicals, said sulfolane having 4 to 12 carbon atoms per molecule, and
   b. removing a first stream consisting essentially of n-butane and being essentially free of acetone and a second stream consisting essentially of sulfolane and acetone from said contacting zone.

2. A process in accordance with claim 1 wherein said second stream is fractionally distilled to produce a third stream consisting essentially of acetone and a fourth stream consisting essentially of sulfolane and being essentially acetone-free.

3. A process in accordance with claim 1 wherein a liquid mixture of n-butane and acetone is contacted with liquid sulfolane.

4. A process in accordance with claim 1 further comprising
   a. extractively distilling a second mixture consisting essentially of n-butane and butylenes in an extractive distillation zone with an extractive solvent consisting essentially of a mixture of acetone and a sulfolane having the general formula

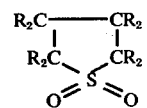

wherein the radicals R which can be the same or different are individually selected from the group consisting of hydrogen, alkyl radicals having 1 to 4 carbon atoms, cycloalkyl radicals having 3 to 6 carbon atoms, and phenyl, which radicals R in turn can be unsubstituted or substituted by alkyl, cycloalkyl and aryl radicals, said sulfolane having 4 to 12 carbon atoms per molecule, to produce an overhead stream consisting essentially of n-butane and some acetone and a fifth stream consisting essentially of sulfolane, acetone and butylenes, and
   b. contacting said overhead stream as said first mixture with said sulfolane in said contacting zone to produce said first and second streams.

5. A process in accordance with claim 4 wherein said extractive solvent consists essentially of 60 to 80 weight percent sulfolane and 40 to 20 weight percent acetone.

6. A process in accordance with claim 4 wherein said fifth stream is fractionated into a hydrocarbon stream consisting essentially of butylenes and a sixth stream consisting essentially of sulfolane and acetone.

7. A process in accordance with claim 6 wherein said sixth stream is recycled into said extractive distillation zone as part of said extractive solvent.

8. A process in accordance with claim 7 wherein said second stream is fractionally distilled to produce a third stream consisting essentially of acetone and a fourth stream consisting essentially of sulfolane, and wherein said third stream consisting essentially of acetone and said sixth stream consisting essentially of sulfolane and acetone are mixed to form a seventh stream, and wherein said seventh stream is introduced into said extractive distillation as said extractive solvent.

* * * * *